United States Patent
Tavanti et al.

(10) Patent No.: US 9,622,715 B2
(45) Date of Patent: Apr. 18, 2017

(54) CLINICAL AMBIENT CONTROL SYSTEM

(75) Inventors: Monica Tavanti, Eindhoven (NL); Yi Zhang, Eindhoven (NL); Njin-Zu Chen, Eindhoven (NL); Aaldert Jan Elevelt, Best (NL); Annemarie Christin Yvonne Van Asbeck-Metselaar, 's-Hertogenbosch (NL)

(73) Assignee: Koninklijke Philips N.V., Eindhoven (NL)

( * ) Notice: Subject to any disclaimer, the term of this patent is extended or adjusted under 35 U.S.C. 154(b) by 805 days.

(21) Appl. No.: 13/979,853

(22) PCT Filed: Jan. 24, 2012

(86) PCT No.: PCT/IB2012/050324
§ 371 (c)(1),
(2), (4) Date: Jan. 20, 2014

(87) PCT Pub. No.: WO2012/101577
PCT Pub. Date: Aug. 2, 2012

(65) Prior Publication Data
US 2014/0137326 A1    May 22, 2014

(30) Foreign Application Priority Data
Jan. 26, 2011 (EP) .................................... 11152159

(51) Int. Cl.
*A61B 6/04* (2006.01)
*H05B 37/02* (2006.01)

(52) U.S. Cl.
CPC ....... *A61B 6/0407* (2013.01); *H05B 37/0245* (2013.01)

(58) Field of Classification Search
CPC ..................................................... A61B 6/04
USPC ..................................... 5/601; 378/4, 20–23
See application file for complete search history.

(56) References Cited

U.S. PATENT DOCUMENTS

| 4,629,989 A | 12/1986 | Riehl et al. |
| 5,212,717 A * | 5/1993 | Hada ..................... A61B 6/032 250/491.1 |
| 5,526,245 A | 6/1996 | Davis et al. |
| 5,548,215 A | 8/1996 | Kohno et al. |
| 5,696,574 A * | 12/1997 | Schwaegerle ........... A61B 3/18 108/139 |
| 6,045,262 A | 4/2000 | Igeta et al. |

(Continued)

FOREIGN PATENT DOCUMENTS

| CN | 1842301 A | 10/2006 |
| DE | 102008039791 | 3/2010 |

(Continued)

*Primary Examiner* — Fredrick Conley

(57) ABSTRACT

The invention relates to a system (100) for automating adjustment or adaptation of devices (141-143) such as light, computer programs and positioning of devices used during patient examination. The patient examination is performed by use of a scanner system where the patient is lying on a bed (102) which can be moved into a scanner zone of the scanner where the scanning can be performed and away from the scanner zone. The automated control is achieved by detecting the position of the bed and using the detected position for adjusting or adapting the state, i.e. the function or working of one or more devices (141-143).

17 Claims, 2 Drawing Sheets

(56) References Cited

U.S. PATENT DOCUMENTS

| | | |
|---|---|---|
| 6,264,329 B1 | 7/2001 | Brooks et al. |
| 6,575,575 B2 | 6/2003 | O'Brien et al. |
| 6,773,161 B2 | 8/2004 | Tanaka |
| 7,250,922 B2 | 7/2007 | Sakaniwa |
| 7,293,308 B2 | 11/2007 | Everett et al. |
| 7,702,375 B2 | 4/2010 | Boninger et al. |
| 7,852,080 B2 | 12/2010 | Takamori et al. |
| 2002/0163624 A1 | 11/2002 | O'Brien et al. |
| 2008/0204017 A1 | 8/2008 | Takamori et al. |
| 2009/0080186 A1 | 3/2009 | Helmreich et al. |
| 2014/0137326 A1 | 5/2014 | Tavanti et al. |

FOREIGN PATENT DOCUMENTS

| | | |
|---|---|---|
| JP | H06169907 A | 6/1994 |
| JP | 2003135404 A | 5/2003 |
| JP | 2004243981 A | 9/2004 |
| JP | 2007044353 A | 2/2007 |
| JP | 2009189388 A | 8/2009 |
| JP | 2009240660 A | 10/2009 |

* cited by examiner

CLINICAL AMBIENT CONTROL SYSTEM

FIELD OF THE INVENTION

The invention relates to a control system for controlling appliances, in particular to such a control system for use with a patient scanner.

BACKGROUND OF THE INVENTION

Patient examination by use of scanners such as MR, CT and ultrasound scanners involves different processes. During the examination various appliances such as computer screens may be used in different ways depending on the progress of the examination. Therefore, the clinical personnel may need to adjust the appliances, such as the location of the computer screen, during the examination. The adjustment of appliances may be time consuming and inconvenient for the examination.

Accordingly, it is a problem that clinical personnel may not be able to focus fully on the examination itself, but may also need to perform adjustments and adaptations of various appliances used in the scanner room.

U.S. Pat. No. 6,264,329 discloses a uniquely position adjustable ophthalmic instrument support table for use in conjunction with an examining chair and a lighting system which allows the user to program the desired room lighting independently for each of several inputs such as instrument switches, examination lights or other electrical devices used during an ophthalmic examination. The ophthalmic instrument support table includes a base unit and a table top mounted to the base unit by support structure operates with an infrared control to allow four degrees of freedom to adjust the location of the table top with respect to both the patient seated in the chair and the doctor examining the patient on the opposite side of the table. The lighting control system allows one or two circuits of room lights to be adjusted in intensity and to have this adjustment automatically recalled to set the programmed room lighting condition upon activation of the input.

Whereas U.S. Pat. No. 6,264,329 discloses a system which may automate adjustment of e.g. lights, there is still a need for improvements in relation to examination by use of scanners and, therefore, the inventor has devised the present invention.

SUMMARY OF THE INVENTION

It would be advantageous to achieve improvements for patient examination using scanners. It would also be desirable to enable automation of adjustment actions of appliances during which are required during the examination. In general, the invention preferably seeks to remedy one or more of the above mentioned problems singly or in any combination. In particular, it may be seen as an object of the present invention to provide a system that solves the above mentioned problems, or other problems, of the prior art.

To better address one or more of these concerns, in a first aspect of the invention an ambient control system for use with a bed of a patient scanner is presented where the bed is moveable relative to the scanner, and where the system comprises
- a sensor for detecting a position of the bed and for generating a sensor signal indicative of the position of the bed,
- a controller for controlling a state of an appliance in dependence of the sensor signal by generation of a control signal from the sensor signal for invoking a change of the state of the appliance.

By using the bed position for controlling appliances, e.g. lights or computer screens, the state of the appliances may be optimally adapted to the various processes of the patent examination since various processes may be associated with a particular position of the bed relative to the scanner.

The appliance or one of the appliances may be a position actuator for adjusting the position of a computer screen, a light or a computer which is used for running a computer program where a state of change of the computer program may be invoked by the control signal.

The controller may be configured to generate different control signals from the sensor signal for control of different appliances. Thus, first and second control signals may be generated from a single sensor signal in order to control possibly different first and second appliances, such as a light and a position actuator of a monitor. The first and second control signals may be outputted from the controller via a single output by time-multiplexing the first and second control signals or the first and second control signals may be outputted via respective first and second controller outputs.

In an embodiment a first value of the control signal is for invoking a first change of the state of the appliance and a second value of the control signal is for invoking a second change of the state of the appliance. The first change of the state is different from the second change of state. For example, the first change of state may be an increase of a light intensity of a light and the second change of state may be a decrease of a light intensity of the same light. Accordingly, a plurality of different changes of a state of an appliance may be controlled in dependence of the bed position.

In an embodiment the controller is configured to enable the change of a state of the appliance to be preset. Accordingly, the user may preset a desired change of a state of an appliance. For example, the user may have a preferred position of a computer monitor for a given examination process that can be preset, e.g. by programming the controller. The controller may have recording process, where preferred changes of a state can be recorded by the controller.

In an embodiment the control system comprises an input device connectable with the controller, where the input device enables real time modification of a state of an appliance. By use of an input device such as a computer keyboard, the clinical personnel may be able to overrule any states currently determined from the bed position. For example, an increase of light intensity may be required at a given situation where the bed is in a position which instructs the controller to generate a relative low intensity of light.

In an embodiment the control signal is supplied directly to the appliance via an output of the controller. Thus, the control signal may be in a form which is directly applicable by a device. For example, the control signal may be a high voltage signal capable of powering a light.

In an embodiment the ambient control system further comprises an appliance driver configured to generate a drive signal for the appliance in dependence of the control signal. A driver may transform the control signal from the controller into a signal suitable for powering an appliance, e.g. a light or a position actuator.

A second aspect of the invention relates to a bed system for use with a patient scanner, where the bed system comprises the ambient control system according to the first aspect, and a bed configured so that the position of the bed can be detected by the sensor.

A third aspect of the invention relates to a method for controlling one or more appliances in dependence of a position of a bed relative to a patient scanner, the method comprising:

generating a sensor signal indicative of the position of the bed using a sensor arranged relative to the bed, generating one or more control signals from the sensor signal, and using the one or more control signals to change a state of the one or more appliances.

In an embodiment the one or more control signals are used for controlling one or more of: light intensity of one or more lights, an illumination direction of a light, orientation and/or position of a computer display, visualization mode of computer display information/graphics, audio information or music.

In summary the invention relates to a system for automating adjustment or adaptation of devices such as light, computer programs and positioning of devices used during patient examination. The patient examination is performed by use of a scanner system where the patient is lying on a bed which can be moved into a scanner zone of the scanner where the scanning can be performed and away from the scanner zone. The automated control is achieved by detecting the position of the bed and using the detected position for adjusting or adapting the state, i.e. the function or working of one or more devices.

In general the various aspects of the invention may be combined and coupled in any way possible within the scope of the invention. These and other aspects, features and/or advantages of the invention will be apparent from and elucidated with reference to the embodiments described hereinafter.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
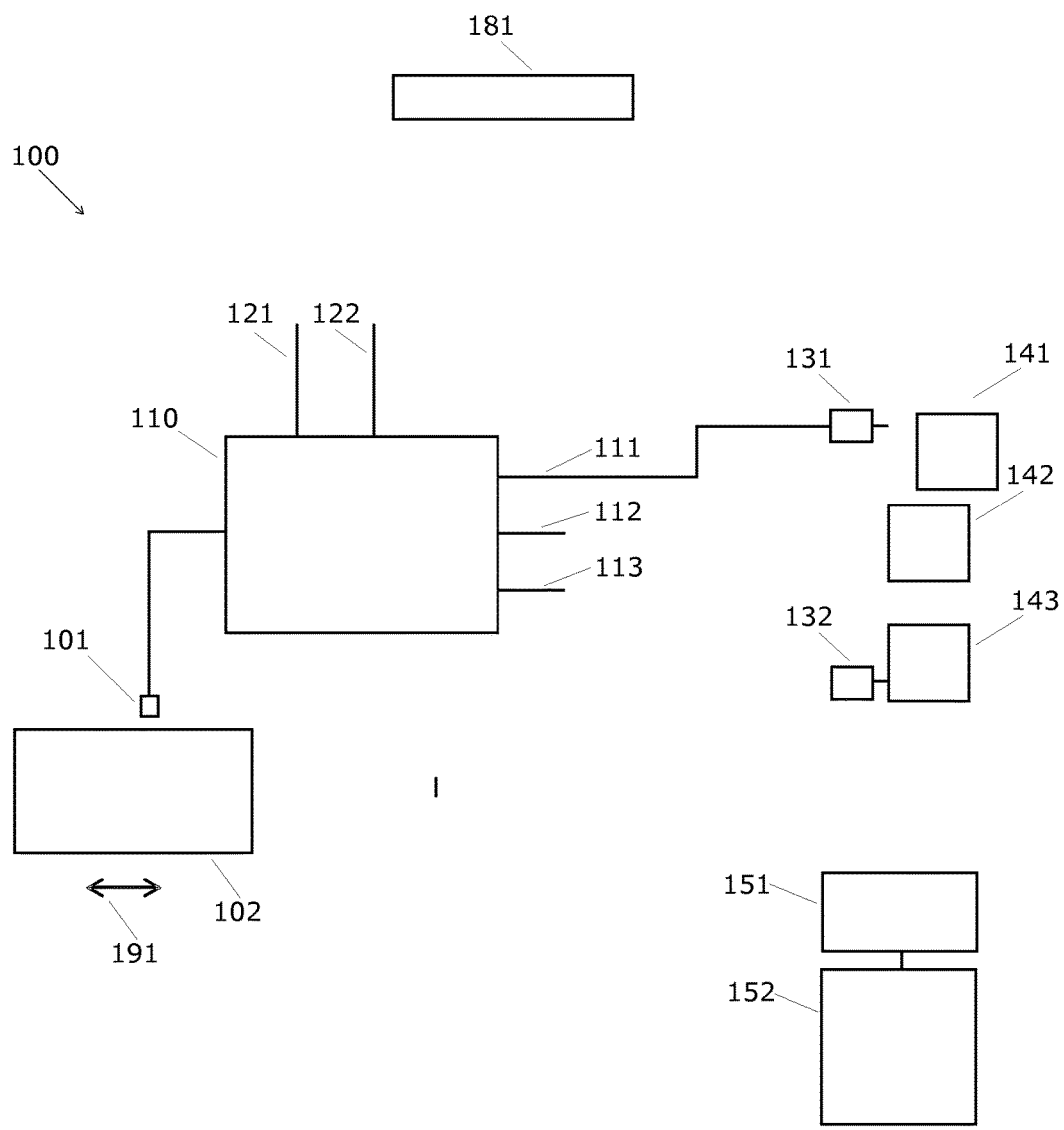
FIG. 1 shows components of an ambient control system.

FIG. 1 shows an ambient control system 100 for use with a bed 102 of a patient scanner such as an MR scanner or other present or future scanners where the patient is located on a bed which is moveable relative to the scanner, e.g. along the longitudinal direction 191 of the patient lying on the bed 102.

The system comprises a bed sensor 101 which is capable of sensing the position of the bed or movement of the bed. For example the bed sensor may be an optical sensor capable of detecting one or more positions of the bed. For example, the bed may be provided with reflecting items which are detectable by the optical bed sensor. Mechanical contact sensors or other types of sensors, for example an encoder connected to the motor used for driving the bed may also be used.

The output of the bed sensor 101 is connected to an input of a controller 110. The controller 110 has one or more outputs 111-113 provided for supplying a control signal to one or more appliances 141-143 comprising lights, actuators for adjusting the position of e.g. computer screens or lights.

The control signal may be supplied directly to the appliance via an output 111-113 of the controller or via an appliance driver 131-132 configured to generate a drive signal for the appliance in dependence of the control signal. For example, the appliance driver may be a light dimmer capable of generating a high voltage signal for a light in dependence of a low voltage control signal, where e.g. the amplitude of the voltage of the control signal determines the light intensity of the light connected to the light dimmer.

The appliance driver could also be an actuator driver capable of converting the low voltage control signal to an actuator power signal. For the purpose of controlling an actuator, the control signal may be an analog or digital reference position which is supplied the actuator driver 132 which supplies the actuator power signal to the position actuator until the desired reference position has been achieved. In practice, the actuator may contain a position detector such as an encoder which transmits the position signal back to the driver as a feedback signal for controlling the position actuator in a feedback loop.

A required driver 131 may be a separate component which is connectable to the controller 110 and one of the appliances appliance or it may be integrated with the controller 110 or the appliance 141. Accordingly, the control signal generated by the controller may be a control signal which has been conditioned (e.g. converted to a high voltage signal) by a driver 131 comprised by the controller 110, or the control signal may be a low voltage signal which needs to be conditioned by a separate driver or a driver comprised by an appliance such as a position actuator which has a built-in driver. The control signal generated by the controller may not need to be modified by a driver, e.g. the controller may generate a control signal which is directly applicable by a computer.

Thus, the controller 110 may generate a plurality of control signals of different formats as described above, which control signals may be transmitted by one or more of the outputs 111-113. Thus, one output may be able to transmit different control signals of different formats, e.g. by use of time shifted transmission, i.e. time multiplexing.

In addition to controlling appliances 141-143 such as lights and position actuators, a control signal may be generated by the controller 110 from the bed position to control the graphical user interface displayed by a computer monitor 152, e.g. for changing states or modes of visualization of the a graphical user interface of a computer program run by a computer and displayed on a computer display. For that purpose a control signal which is indicative of the position of the bed 102 may be supplied to a computer 151 running a computer program with an associated graphical user interface displayed on a monitor 152.

As an example, the light intensity of a light 141 can be controlled by a control signal from the controller 110, where a first value of the control signal is for increasing the light intensity of the light and second value of the control signal is for decreasing light intensity. Thus, a first position of the bed may cause generation of the first value of the control signal, and a second position of the bed may cause generation of the second value of the control signal.

In general the appliances have different states for example in the form of different light intensities and/or different light colors of lights, different positions and/or directions of lights and computer screens, and different visualization modes of a graphical user interface, i.e. different views of a graphical user interface of a computer program.

Accordingly, the controller is configured for controlling a state of an appliance in dependence of the sensor signal by generation of a control signal from the sensor signal for invoking a change of the state of the appliance. A change of a state of an appliance may be a change of light intensity, a change of light color, a change of position or orientation of a position actuator, or a change of the appearance or visualization mode of a graphical user interface.

The controller 110 may comprise a computer or similar data processor for generating a control signal in dependence of the output signal from the bed sensor. For example, the bed may have two positions and, consequently, the bed sensor is capable of generating distinguishing signals in dependence of the two positions. When the bed is in the first position, the controller may generate a first control signal with a first value supplied via a first output 111 to a light appliance, which first value is for invoking or changing the light intensity to a first light intensity. Simultaneously, when the bed is in the first position, the controller may generate a second control signal with a first value supplied via a second output 112 for controlling the position and/or orientation of a position actuator of a computer screen according to the first value of the second control signal.

When the bed is in the second position the controller may generate the first control signal with a second value supplied via the first output 111 to a light appliance, which second value is for changing the light intensity to a second light intensity being different from the first light intensity. Simultaneously, when the bed is in the second position, the controller may generate a second control signal with a second value supplied via the second output 112 e.g. for invoking or changing the position of the actuator into a position associated with the second value.

The controller 110 or the processor unit of the controller may be able to run a computer program which includes rules for changing states of appliances in dependence of the bed position, i.e. in dependence of the signal from the bed sensor, as exemplified above.

The controller 110 may have one or more additional inputs 121, 122 for receiving input signals from other sensors, devices such clinical devices or user input devices such as a computer keyboard. Thus, the generation of a control signal from the bed sensor 101 may be further dependent on input signals from other inputs 121, 122.

For example, when a user input device 181 such as a keyboard or other user operable buttons is connected to one or more inputs 121, the control signal may be determined solely in dependence of the signal from the user input device or in combination from the signal from the user input device 181 and the bed position sensor. For example, an input device 181 may be provided to enable the clinical personnel to manually select a given light intensity completely independent of the bed position by configuring the controller 110 to overrule the bed sensor input when a predetermined value of a signal is received from a user input device 181 via one of the auxiliary input 131-132. As another example, the controller 110 may be configured to modify the control signal otherwise determined in dependence solely of the bed position input signal, by enabling the clinical personnel to preset a change of a state of one or more appliances, for example by providing a selection of different selectable state changes or states of one or more appliances such as a selection of different selectable actuator positions and/or light intensity settings of positions actuators and lights. In this way the clinical personnel is able to preset preferred user defined state changes or states of different appliances that will be invoked when the bed 102 enters a given position.

Instead of or in addition to enabling presetting of state changes, the input device 181 may enable real time modification of a state of an appliance, e.g. the light intensity of a light. For that purpose the controller 110 may be configured so that when a signal having a particular value is received or when a signal is received from a particular input 121-122, then a control signal is generated for changing a state of an appliance independently of the bed position.

The bed 102 may be a special bed configured so that the position of the bed can be detected by the position sensor 101, or the bed may be a normal bed provided with e.g. reflective items detectable by the positions sensor. Thus, the bed may be comprised by the ambient control system 100. Similarly, any of the appliances 141-143, e.g. special lamps, and drivers 131-132 may be comprised by the ambient control system 100. However, it is also possibly that the appliances are not part of the control system.

Figure 2:
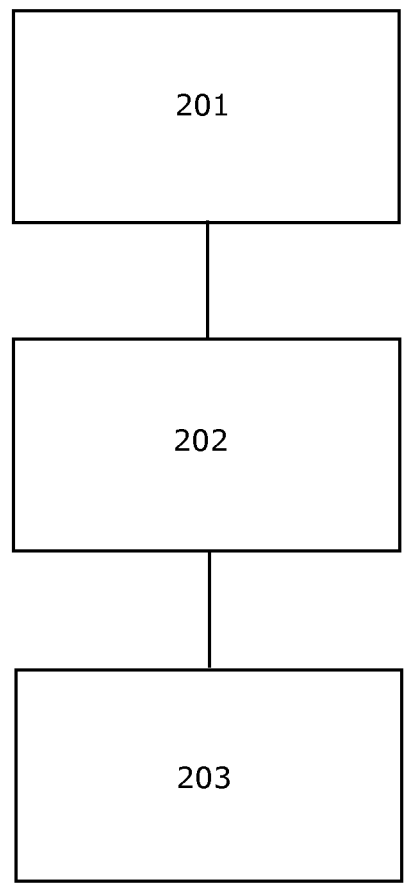
FIG. 2 illustrates method steps according to an embodiment of the invention.

FIG. 2 shows the following method steps according to an embodiment of the invention:
- step 201: generating a sensor signal indicative of the position of the bed using a sensor arranged relative to the bed,
- step 202: generating one or more control signals from the sensor signal, and
- step 203: using the one or more control signals to change a state of the one or more appliances.

Other embodiments of the invention may include other steps such as generating the one or more control signals in dependence of other input signals such as input signals from a user operable input device, e.g. a computer keyboard.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage.

A computer program for use with the controller for generation of control signals in dependence of the sensor signal may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An ambient control system for use with a bed of a patient scanner, where the bed is moveable relative to the scanner, and where the system comprises:

a sensor configured to detect a position of the bed and configured to generate a sensor signal indicative of the position of the bed, a controller programmed to control a position of a position actuator in dependence of the sensor signal by generation of a control signal from the sensor signal for causing a change of the position of the position actuator from a first position to a second position;

wherein the controller is programmed to generate a first value of the control signal for causing a first change of the position of the position actuator and a second value of the control signal for causing a second change of the position of the position actuator.

2. The ambient control system according to claim 1, where the controller is programmed to generate different control signals from the sensor signal for control of at least one appliance other than the position actuator.

3. The ambient control system according to claim 2, wherein the at least one appliance other than the position actuator is a computer display or a light source.

4. The ambient control system according to claim 1, where the controller is programmed to enable a change in the position of the position actuator to be preset.

5. The ambient control system according to claim 1, where the ambient control system further includes at least one input device connectable with the controller, where the input device enables real time modification of the position of the position actuator.

6. The ambient control system according to claim 1, wherein the controller further includes an output programmed to supply the control signal directly to the position actuator.

7. The ambient control system according to claim 1, where the ambient control system further comprises an appliance driver configured to generate a drive signal for the appliance in dependence of the control signal, the appliance driver being configured to convert a low voltage control signal to an actuator power signal which is supplied to the position actuator.

8. A bed system for use with a patient scanner, where the bed system comprises the ambient control system according to claim 1, a bed configured so that the position of the bed is detected by the sensor.

9. An ambient control system for use with a bed of a patient scanner, the bed being moveable relative to the scanner, the system comprising:

a sensor configured to detect a position of the bed and configured to generate a sensor signal indicative of the position of the bed;

a light dimmer; and a controller programmed to control a light intensity of a light source by generating a control signal dependent on the sensor signal, the control signal being sent to the light dimmer for causing a change of the light intensity of the light source from a first light intensity to a second light intensity.

10. A bed system for use with a patient scanner, wherein the bed system comprises the ambient control system according to claim 9, a bed configured so that the position of the bed is detected by the sensor.

11. The ambient control system according to claim 9, wherein the light dimmer is configured to generate a high voltage signal for the light source in. dependent of a low voltage control signal and supply the high voltage signal to the light source.

12. The ambient control system according to claim 9, wherein the controller is further programmed to generate different control signals from the sensor signal for control of the light source and at least one appliance other than the light source.

13. The ambient control system according to claim 12, wherein the at least one appliance other than the light source is a computer display or a position actuator.

14. The ambient control system according to claim 9, wherein the control signal includes a first value of the control signal for causing an increase of the light intensity of the light source and a second value of the control signal for causing a decrease of the light intensity of the light source.

15. The ambient control system according to claim 9, wherein the change in the light intensity of the light source is preset by the controller.

16. The ambient control system according to claim 9, wherein the ambient control system further includes at least one input device connectable with the controller, the input device enabling real time modification of the light intensity of the light source.

17. The ambient control system according to claim 9, wherein the controller is further programmed to supply the control signal directly to the light source.

\* \* \* \* \*